United States Patent
Goulas et al.

(10) Patent No.: US 7,368,694 B2
(45) Date of Patent: May 6, 2008

(54) DEVICE FOR MEASURING LIGHT ABSORPTION CHARACTERISTICS OF A BIOLOGICAL TISSUE SAMPLE

(75) Inventors: Yves Goulas, Le Plessis (FR); Zoran Cerovic, Paris (FR); Ismaël Moya, Gif sur Yvette (FR)

(73) Assignee: Centre National De La Recherche Scientifique (C.N.R.S), Paris (FR)

( * ) Notice: Subject to any disclaimer, the term of this patent is extended or adjusted under 35 U.S.C. 154(b) by 863 days.

(21) Appl. No.: 10/490,943

(22) PCT Filed: Aug. 20, 2002

(86) PCT No.: PCT/FR02/02912

§ 371 (c)(1),
(2), (4) Date: Jul. 13, 2004

(87) PCT Pub. No.: WO03/029791

PCT Pub. Date: Apr. 10, 2003

(65) Prior Publication Data

US 2004/0233448 A1   Nov. 25, 2004

(30) Foreign Application Priority Data

Sep. 28, 2001  (FR) .................................. 01 12551

(51) Int. Cl.
- *G01J 1/32* (2006.01)
- *G01N 21/00* (2006.01)
- *A61B 5/00* (2006.01)

(52) U.S. Cl. .................. 250/205; 356/434; 600/310
(58) Field of Classification Search ............... 250/205; 356/432–434, 436; 600/310

See application file for complete search history.

(56) References Cited

U.S. PATENT DOCUMENTS

| | | | | |
|---|---|---|---|---|
| 3,799,672 A | * | 3/1974 | Vurek | ........................ 356/41 |
| 4,863,265 A | * | 9/1989 | Flower et al. | ................ 356/41 |
| 4,942,877 A | * | 7/1990 | Sakai et al. | ................. 600/323 |
| 5,096,294 A | | 3/1992 | Layzell et al. | |
| 5,800,348 A | | 9/1998 | Kaestle | |

FOREIGN PATENT DOCUMENTS

| | | |
|---|---|---|
| DE | 35 18 527 | 11/1986 |
| EP | 0 502 717 | 9/1992 |
| WO | 00/75642 | 12/2000 |

* cited by examiner

*Primary Examiner*—Thanh X. Luu
*Assistant Examiner*—Stephen Yam
(74) *Attorney, Agent, or Firm*—Young & Thompson

(57) ABSTRACT

A device includes an element (7) for illuminating the sample (1), alternately emitting first and second radiation beams; device (9) for receiving and analyzing radiation derived from the sample (1) which converts the output radiation into control signal (S0); monitoring and controlling device (31) emitting first (S1) and second (S2) signals controlling the illuminating means (7), and a measuring signal (Sm); and device for calculating absorption characteristics of the sample (1), on the basis of the measuring signal (Sm). The monitoring and control elements (31) are adapted so that, after at least one period (Tp) of variation of the radiation beams, the amplitude of the control signal (S0), sensed on emitting phases, is equal to the amplitude of the control signal (S0), sensed on emission phases of the other radiation, and the measuring signal (Sm) represents at least one of the control signals (S1, S2).

31 Claims, 7 Drawing Sheets

DEVICE FOR MEASURING LIGHT ABSORPTION CHARACTERISTICS OF A BIOLOGICAL TISSUE SAMPLE

The invention relates to a device for measuring light absorption characteristics of a biological tissue sample.

In particular, the invention is intended to analyse the content of plant leaves, namely the concentration of certain chemical compounds.

During their life cycle plants must adapt to variations, which are often substantial, in their environmental conditions, such as for example the light or the availability of water and of mineral resources. These adaptations often accompany variations in the content in the leaves of certain metabolites, in particular those of the so-called secondary metabolism such as polyphenols. This class of metabolites designates the compounds which have at least one phenol function or which are directly derived from phenolic compounds, for example by esterification. Another usual designation which we will use in the following for these compounds and those of related families is the name "phenylpropanoids" because of their biosynthetic origin.

It has been established that the phenylpropanoids vary from one species to another, that they accumulate principally in the vesicles of the epidermal cells and that they can exhibit significant variations of concentration as a function of the environmental conditions.

For example, M. M. Cadwell et al have shown in an article entitled "Internal filters: prospects for UV-acclimation in higher plants" (Physiol. Plant (1983) 58, pp. 445-450) that phenylpropanoids accumulate following exposure to light, probably with the aim of protecting the leaves from ultraviolet radiation.

Another reason also advanced for the variations of the phenylpropanoid content of the leaves involves the adjustment of the metabolic processes as a function of the relative proportions of the carbon and nitrogen resources available. When nitrogen is abundant relative to the quantity of fixed carbon, the plant invests in the production of nitrogen-consuming biomass which favours its growth. The result is a small proportion of phenylpropanoids. When nitrogen is rarefied relative to the carbon, photosynthetic production is then diverted towards the synthesis of compounds which are low in nitrogen such as phenylpropanoids. Reference may be made in this connection to the article in the journal Oikos (1983, vol. 40, pp. 357-368) by J. P. Bryant et al "Carbon/nutrient balance of boreal plants in relation to vertebrate herbivory"; in "Journal of Chemical Ecology" (1989, vol. 15, pp. 1117-1131) the article by P. Price et al "Carbon-nutrient balance hypothesis in within-species phytochemical variation of Salix lasiolepsis"; in the journal "Quart. Rev. Biol." (1992, vol. 67, pp. 283-335) the article by D. A. Herms and W. J. Mattson "The dilemma of plants: To grow or to defend".

Other roles of the phenylpropanoids have also been shown, such as the selection of food by herbivores or protection against pathogenic agents (Plant Cell, 1995, vol. 7, pp. 1085-1097, R. A. Dixon and N. K. Paiva, Stress-induced phenylpropanoid metabolism).

Thus the sequence in situ of the phenylpropanoid content of the leaves or the epidermis of the leaves would provide information which can be used in different fields of application. In ecophysiology it would make it possible to follow the effects of the increase in the UV radiation due to the hole in the ozone layer and the effects of the increase in the atmospheric $CO_2$ content due to the use of fossil hydrocarbons and to study the interactions between plants and herbivores. In plant biology it would make it possible to evaluate the productivity of the secondary metabolism and to follow the plant development. In arboriculture a tool would be available for description of the plant structure which could quantify the distribution of the light within the foliage or could even estimate the distribution of the nutritional resources. Finally, in agriculture a tool would be available for fast non-invasive diagnosis for control of the supply of nutrients or attack by pathogenic agents.

A known process for analysis of the phenylpropanoid content consists first of all of extracting these foliar pigments by grinding and immersion in a solvent, such as methanol for example. Then the phenylpropanoid content of the extract is determined by measurement of the transmittance in ultraviolet where phenylpropanoids have one of several absorption bands. (On this subject see "Analysis of Phenolic Plant Metabolites. Methods in Ecology" by P. G. Waterman and S. Mole, eds. J. H Lawton and G. E. Likens, 1994, Oxford: Blackwell Scientific Publications, 238). However, this latter process is destructive and is not applicable in the field because of the laboratory equipment which it requires. Measurement in situ by ultraviolet absorption is no longer applicable because of the high absorption of photosynthetic pigments (chlorophyll a and b) which interferes with the absorption due to the phenylpropanoids which is to be measured.

In order to be used in the field within the framework of these different applications, the measurement of the phenylpropanoid content must be fast and simple and must be capable of being carried out in situ in a non-destructive manner in order to permit regular follow-up.

Also an advantageous method of evaluation in situ consists of determining the transmittance of the epidermis of the leaves on the basis of measurements of the red fluorescence originating from the chlorophyll excited by ultraviolet radiation for analysis on the one hand and excited by visible reference radiation on the other hand.

Thus at the analysis wavelength $\lambda 1$ the measured fluorescence F1 is:

$$F1 = k1\ T1\ I1$$

where T1 is the transmittance of the epidermis at the wavelength $\lambda 1$, I1 is the intensity of the incident measurement radiation at the same wavelength, and k1 is a proportionality factor.

At the reference wavelength $\lambda 0$ the measured fluorescence F0 is determined by an analogous equation:

$$F0 = k0\ T0\ I0$$

where T0 is the transmittance of the epidermis at the wavelength $\lambda 0$, I0 is the intensity of the incident measurement radiation at the same wavelength, and k0 is a proportionality factor.

The absorbance A due to the phenylpropanoids present in the epidermis is determined by the relationship:

$$A = -\mathrm{Log}[T1/T0] = -\mathrm{Log}[F1/F0 \times (I0\ k0)/(I1\ k1)] \quad (1)$$

and if I1, k1 and k0 are kept constant from one measurement to another:

$$A = -\mathrm{Log}[F1/F0] + C, \text{ where } C \text{ is a constant.}$$

As the absorbance and phenylpropanoid content vary in a parallel manner, it is therefore possible to estimate the phenylpropanoid content on the basis of the measurements of F1 and F0 and a calibration which determines the value of the constant.

In reality C is dependent not only upon the measuring instrument but also upon the variations in the fluorescence yield of the chlorophyll which may occur between the measurement at the analysis wavelength $\lambda 1$ and the measurement at the reference wavelength $\lambda 0$.

In fact it is well known in photosynthesis and in plant ecophysiology that the quantum yield of chlorophyllian fluorescence varies widely and that it depends in part upon the luminous intensity previously received, by means of photochemical and non-photochemical "quenching" mechanisms.

Consequently the reference measurement at the wavelength $\lambda 0$ is delicate to carry out because it is necessary to be sure that the fluorescent quantum yield of the chlorophyll has not varied or has varied by a known factor between the moment of measurement at the analysis wavelength and the moment of measurement at the reference wavelength.

One procedure is described by P. Bilger et al in an article entitled "Measurement of leaf epidermal transmittance of UV radiation by chlorophyll fluorescence" published in "Physiologia Plantarum" (Vol. 101, pp. 754-763, 1997). The authors use a fluorimeter called "Xe-PAM" sold by Walz (Effeltrich, Germany). In order to obtain a stable state of fluorescence yield of the chlorophyll, they carry out the measurement on leaves adapted to darkness and reduce the intensity of the analysis and reference light beams. However, this results in an extremely long measurement time (in order to ensure a good signal-to-noise ratio) which is divided into 30 mins of adaptation to the darkness and 2 mins of actual measurement. Therefore such a device is not adapted to use in the field.

Therefore the invention relates more precisely to a device for measuring the light absorption characteristics of a biological tissue sample comprising:

means for illumination of the sample adapted to emit alternately at least one first and one second light radiation beam towards the sample, the said radiation beams having respectively a first and a second wavelength which are different from one another;

means for reception and analysis of the output light radiation emitted by the sample, the said reception and analysis means comprising means for converting the said output radiation into a control signal;

monitoring and control means which receive the monitoring signal as input and emit at the output at least the first and the second signals for controlling the illuminating means, corresponding to the first and second radiation beams respectively, and at least one measurement signal; and means for computing the absorption characteristics of the sample which are adapted to receive the said measurement signal as input and to compute the said characteristics as a function of the said measurement signal.

One of the principal objects of the invention is to provide such a device which is light, portable, easy to use in the field, and which makes it possible to carry out quickly and with great precision a large number of samplings for routine measurements in such a way as to make it possible, in a first particularly advantageous application, to evaluate in vivo the content of compounds of the family of phenols or phenylpropanoids in the epidermis of the leaves.

Another important object of the invention is to produce a device which is of simple design, low cost and is easy to use.

To this end, in a measuring device of the type set out above, the monitoring and control means are adapted so that the light intensity of each of the radiation beams varies in a periodic manner, phase-shifted with respect to one another, and so as to regulate at least one of the control signals as a function of the monitoring signal in such a way that, over an integration time period of at least one period of variation of the said radiation beams, the amplitude of the said monitoring signal taken over the emission phases of one of the radiation beams is equal to the amplitude of the monitoring signal taken over the emission phases of the other radiation beam, and the measurement signal represents at least one of the said control signals over the integration time period.

Thus the fluorescence of a sample can be used as a quantity representing its light absorption characteristics, even if the sample has a variable fluorescence, as is the case for a fluorescent biological sample containing chlorophyll for example. The regulation loop makes it possible to bring about the measurement of these variations.

According to other characteristics of the device according to the invention, taken in isolation or in any technically feasible combination:

the monitoring and control means are adapted to deliver a first control signal such that the amplitude of the light intensity of the first radiation beam is constant, whilst the amplitude of the second signal is regulated by the said monitoring and control means;

the said measurement signal consists of the said second signal over the integration time period;

the illuminating means include first and second light sources which are adapted to emit the first and second radiation beams respectively and are supplied electrically by respective first and second electrical supply means, the said supply means being controlled by the first and second control signals respectively;

at least one of the light sources is a light-emitting diode;

the first light source emits the first radiation beam in a wavelength range corresponding to the ultraviolet range, particularly from 300 to 390 nm, particularly approximately 370 nm;

the second light source emits the second radiation beam in a wavelength range corresponding to the red light range, particularly approximately 670 nm;

the illuminating means include at least one optical filter adapted so as to filter the radiation beams from the light sources emitted towards the sample;

the monitoring and control means include synchronisation means connected to the illuminating means, emitting at least one periodic synchronisation signal towards the said illuminating means in such a way that the light intensity of each of the radiation beams varies in a periodic manner, phase-shifted with respect to one another;

the synchronisation means are adapted so as to cause the light intensity of the first and second radiation beams to vary with a frequency greater than a minimum value substantially equal to 1 kHz;

the monitoring and control means include a monitoring and control device connected to the synchronisation means in such a way as to receive the synchronisation signal, receiving the monitoring signal as input;

the said monitoring and control device includes a high-pass filter adapted so as to filter the monitoring signal at the input;

the said monitoring and control device includes a demultiplexer device which receives as input, on the one hand, a signal representing the monitoring signal and, on the other hand, the synchronisation signal, the said demultiplexer device being adapted so as to supply as output a first elementary signal representing the level of intensity of the output radiation during an emission phase of the first radiation beam and a second elementary signal representing the level of intensity of the output radiation during an emission phase of the second radiation beam;

the demultiplexer device includes at least two switch means controlled alternately for opening and closing by the synchronisation signal, and a memory means associated with each of the said switch means;

the said signal representing the monitoring signal is the monitoring signal filtered by the said high-pass filter;

the monitoring and control device includes a differential amplifier of which the inverting input receives the first elementary signal and the non-inverting input receives the second elementary signal;

the monitoring and control device includes an integrating circuit which is supplied as input with the output signal from the said differential amplifier and is adapted so as to emit an integrated signal over at least one period of the synchronisation signal;

the said integrated signal constitutes the measurement signal;

the converter means include a photodetector which converts an optical signal into an electrical signal and a preamplifier of the electrical signal emitted by the said photodetector;

the reception and analysis means include an optical filter interposed between the sample and the converter means; and the computing means are connected at the output to at least one peripheral, particularly a display screen and/ or a data storage device.

The illumination means can be adapted so as to emit only two radiation beams or, as a variant, the illumination means are adapted to emit alternately three radiation beams of different wavelengths, the monitoring and control means being adapted to deliver three corresponding control signals, a first control signal being such that the amplitude of the light intensity of the first radiation beam is constant, whilst the respective amplitudes of the second and third signals are regulated by the said monitoring and control means.

According to a first embodiment of the invention, the device has a pincer structure comprising two arms articulated on one another in such a way as to be able to grip a sample, the first arm being provided with the illumination means and the second arm being provided with the reception and analysis means.

According to a second embodiment of the invention, the device includes a bundle of optical fibres through which the radiation beam emitted by the illumination means and the radiation beam emitted by the sample pass, this latter radiation beam being a reflected radiation beam.

The invention also relates to a method of measuring the light absorption characteristics of a biological tissue sample, in which the following operations are carried out:

the sample is illuminated by illumination means alternately by first and second radiation beams of different wavelengths and periodic intensities;

the radiation emitted by the sample is detected and the said radiation is analysed;

the said illumination means are controlled as a function of the said detected radiation.

This method is characterised in that the said control is carried out in the following manner:

the intensity of the first and second radiation beams is regulated such that, over an integration time period ($T_i$) of at least one period ($T_p$) of variation of the said radiation beams, the intensity ($I_F$) of the output radiation taken over the emission phases of one of the first and second radiation beams is equal to the intensity ($I_F$) of the output radiation taken over the emission phases of the other one of the first and second radiation beams;

the light absorption characteristics of the sample are calculated as a function of the desired intensity of one of the said first and second radiation beams taken over an integration time period.

According to optional characteristics of the method according to the invention:

the amplitude of the intensity of one of the said first and second radiation beams is kept constant, whilst the amplitude of intensity of the other one of the said radiation beams is regulated; and the radiation emitted by the sample is filtered before it is analysed.

As has been mentioned previously, use of the device or of the method which have been described above consists of measuring the light absorption characteristics of a plant leaf, in particular in order to carry out the measurement of the concentration of compounds of the family of phenols or phenylpropanoids in the epidermis of a leaf.

Such a use can advantageously make it possible to estimate the nutritional needs, particularly in terms of nitrogen, of a culture.

Naturally, the device and the method apply to measurements of the concentration of other chemical compounds. For this it is sufficient to adapt the analysis wavelength, namely the wavelength of one of the luminous radiation beams emitted by the illumination means, to the compounds to be measured.

Other uses of the device or of the method which have been previously described consist of measuring the light absorption characteristics of an animal or human tissue containing haemoglobin derivatives, or carrying out a medical or veterinary diagnosis.

Particular embodiments of the invention which are given by way of non-limiting examples will now be described with reference to the accompanying drawings, in which.

In the following description particular embodiments of the invention will be illustrated which are in particular adapted to the measurement of the phenylpropanoid concentration in the epidermis of a leaf.

Figure 2:
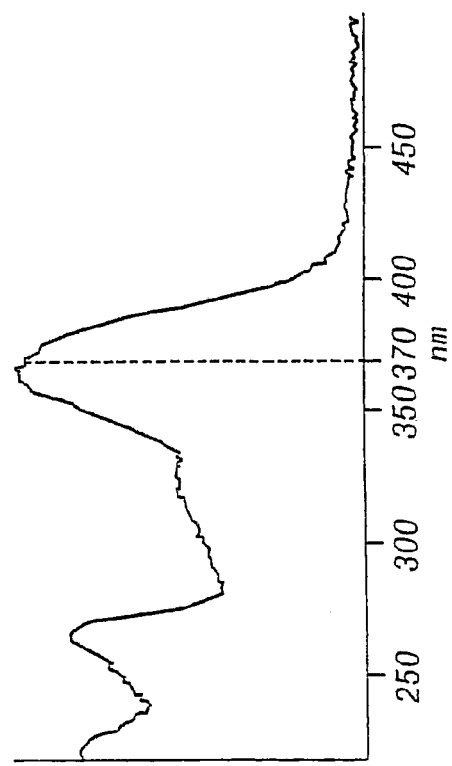
FIG. 2 shows the absorption spectrum of a particular phenylpropanoid, Kaempferol, as a function of the wavelength (given in nanometres) of the incident radiation.
Figure 1:
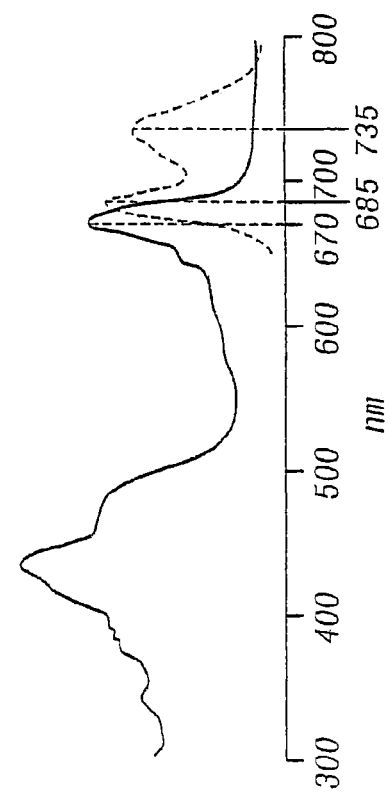
FIG. 1 shows the absorption spectrum of photosynthetic pigments in vivo and the fluorescence spectrum of chlorophyll as a function of the wavelength (given in nanometres) of the incident radiation.

Prior to the detailed description of a device according to the invention, it is useful to mention the optical properties, on the one hand, of photosynthetic pigments in vivo (FIG. 1) and, on the other hand, of a particular phenylpropanoid, Kaempferol, which is chosen by way of example (FIG. 2).

The absorption spectrum of photosynthetic pigments in vivo shows a first absorption peak in the vicinity of 430 nanometres and a second absorption peak in the red light range in the vicinity of 670 nanometres.

The fluorescence spectrum of chlorophyll in vivo (shown by broken lines) shows two peaks very close to approximately 685 nanometres and approximately 735 nanometres.

FIG. 2 shows the absorption spectrum of Kaempferol, which shows a principal absorption peak at approximately 370 nanometres and an absorbance of almost zero for wavelengths greater than 420 nanometres.

Within the scope of use of the invention for measuring the Kaempferol concentration in the epidermis of a plant leaf, the photosynthetic pigments contained in the leaf are used as a sensor emitting, by way of the chlorophyll, a fluorescent radiation in the red in response to an excitation signal consisting of an ultraviolet radiation beam partially absorbed by the compound to be metered which is contained in the epidermis. It will be seen that a reference signal in the visible red range is not absorbed by the phenylpropanoid, such that the absorption of this radiation is only due to the photosynthetic pigments.

Figure 3:
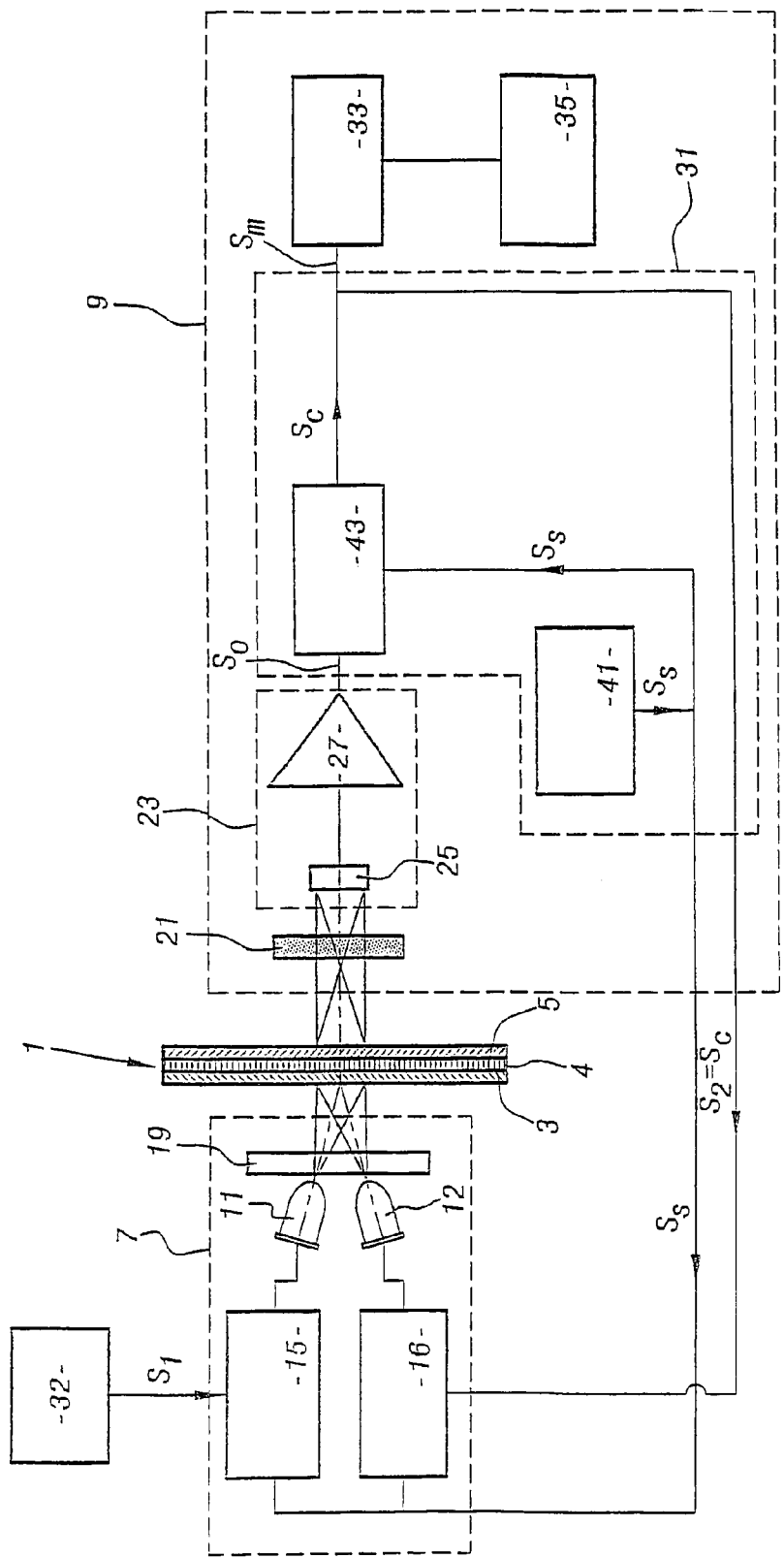
FIG. 3 is an overall block diagram of the measurement device according to the invention in which is placed a sample to be analysed consisting of a plant leaf.

FIG. 3 shows a diagram of a device according to the invention and a sample of biological tissue in respect of which the concentration of an absorbent chemical compound is to be evaluated.

In this particular example the sample 1 is a plant leaf comprising, disposed in superimposed layers, a first layer of epidermis 3, a central layer of tissue which contains chlorophyll 4, and a second layer of epidermis 5.

The device essentially includes means 7 for illumination of the sample 1 and means 9 for reception and analysis of the output light radiation emitted by the sample 1. The illumination means 7 and the reception and analysis means 9 are shown in this particular embodiment on either side of the sample 1, the output light radiation being a radiation beam transmitted by the sample 1.

The illumination means 7 include a first light source 11 and a second light source 12, consisting for example of light-emitting diodes, the first source 11 emitting within a wavelength range corresponding to the ultraviolet range, preferably within the range from 300-390 nm, preferably 370 nm, whilst the second light source 12 emits within a wavelength range corresponding to the red light range, preferably approximately 670 nm. Each source 11, 12 is supplied electrically by a respective electrical supply means 15, 16 and directed towards the location of the sample 1.

A first optical filter 19 is interposed between the light sources 11, 12 and the location of the sample 1 in such a way that the light radiation beams emitted by the sources 11, 12 have a wavelength spectrum concentrated in the vicinity of the principal wavelength, namely 370 nm and 670 nm respectively. Naturally, the filtering of the first light radiation beam emitted by the first source 11, on the one hand, and the second light radiation beam emitted by the second source 12, on the other hand, can be carried out by two separate filters each operating for a given wavelength.

The reception and analysis means 9 include a second optical filter 21 and converter means 23, the second optical filter 21 being interposed between the location of the sample 1 and the converter means 23. Thus the converter means 23 receive the light radiation transmitted by the sample 1 and filtered by the second optical filter 21 in order to eliminate parasitic radiation beams, particularly radiation beams emitted by the first and second sources 11, 12. By virtue of this arrangement only the fluorescent radiation reaches the converter means 23.

The converter means 23 essentially consist of a photodetector 25, which converts the optical signal emitted by the filter 21 into an electrical signal, and a preamplifier 27 of the electrical signal emitted by the said photodetector.

The electrical signal emitted by the converter means 23 and corresponding to the radiation detected at the output of the sample 1 will henceforth be called the "monitoring signal" $S_0$.

The reception and analysis means 9 also include electrical monitoring and control means 31 connected to the converter means 23 in such a way as to receive the monitoring signal $S_0$.

The first electrical supply means 15 is controlled by a control signal $S_1$ emitted by a regulator device 32 in such a way that the intensity delivered by the supply means 15 is constant at a level which may be adjustable. Thus the light intensity delivered by a first source 11 is dependent upon the control signal $S_1$ which in this case is constant.

The regulator device 32 can possibly be provided with a manual control for amplitude adjustment.

The monitoring and control means 31 are connected at the output to the electrical supply means 16 in such a way as to emit thereto a respective control signal $S_2$. Thus the light intensity delivered by the second light source 12 is dependent upon the control signal $S_2$ delivered to the electrical supply means 16 by the monitoring and control means 31.

The monitoring and control means 31 also deliver a measurement signal $S_m$ to a computer 33 adapted to compute the absorption characteristics of the analysed sample 1 as a function of the measurement signal $S_m$.

The computer 33 is preferably connected to a peripheral 35, such as a display screen and/or a data storage device.

The monitoring and control means 31 include synchronisation means 41 and a monitoring and control device 43 having two inputs, of which one is connected to the converter means 23 in such as way as to receive the monitoring signal $S_0$ and the other is connected to the synchronisation means 41 in such a way as to receive the synchronisation signal $S_s$ emitted by the synchronisation means 41. The monitoring and control device 43 also has an output connected to the computer 33 in such a way that the control signal $S_c$ produced by the monitoring and control device 43 is transmitted to the computer 33.

The synchronisation means 41 are also connected to respective inputs of the first electrical supply means 15 and the second electrical supply means 16 in order to transmit the synchronisation signal $S_s$ to them.

In the illustrated example, the measurement signal $S_m$ consists of the control signal $S_c$, which is also transmitted to a second input of the second electrical supply means 16.

The first electrical supply means 15 is for example a pulsed electrical supply means operating with a time base defined by the synchronisation signal, for example a pulse signal with a frequency of the order of 1 kHz or greater than this value. The first control signal $S_1$ which controls the operation of the pulsed supply means 15 is then defined as the synchronisation signal $S_s$, the pulsed supply means 15 delivering to the first light source 11 a square-wave signal (FIG. 5A) of constant amplitude, in such a way that the intensity of the UV radiation emitted in response by the first source 11 has a variable intensity between 0 and a fixed maximum value (or fixed amplitude) according to a square-wave profile.

The operation of the second electrical supply means 16 is adapted to the operation of the pulsed supply 15 with the same time base defined by the synchronisation signal $S_s$ such that the light intensity of the beam emitted by the second light source 12 is variable according to a square-wave profile (FIG. 5B) of the same period $T_p$ between 0 and a maximum peak value modulated by the control signal $S_2$. In the illustrated example the second control signal $S_2$ consists of the control signal $S_c$ emitted by the monitoring and control device 43.

Thus a regulation loop is defined which acts retroactively on the control of the second electrical supply means 16 as a function of the monitoring signal $S_0$ corresponding to the light intensity of the radiation transmitted by the sample.

Figure 4:
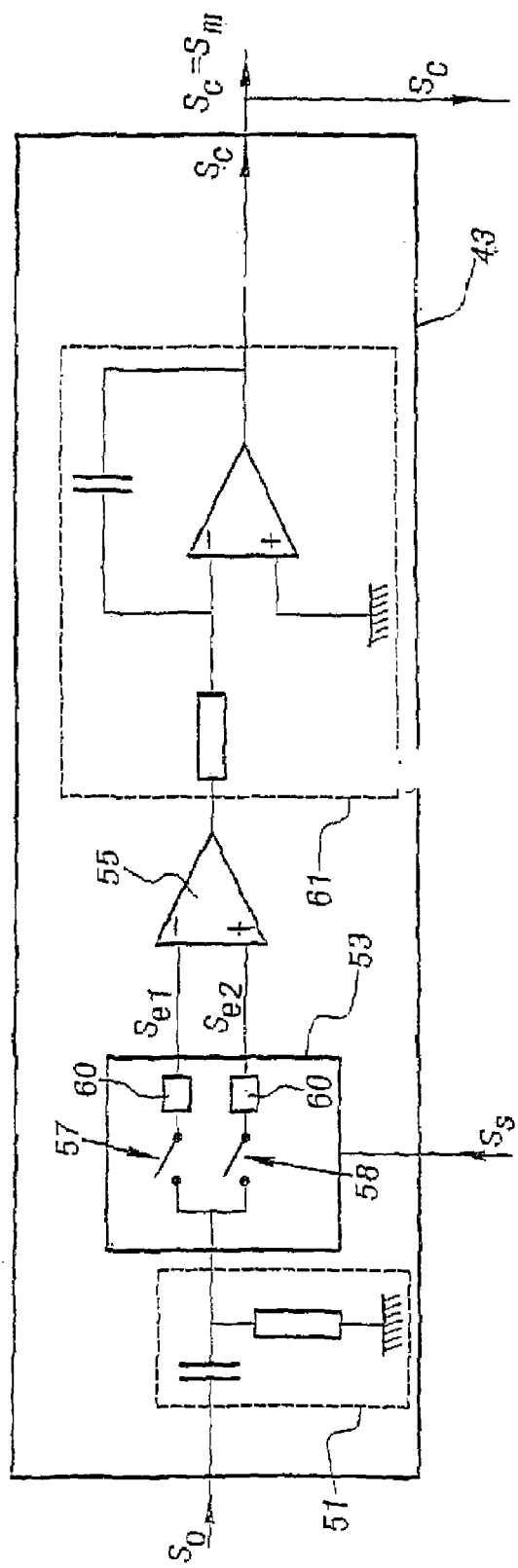
FIG. 4 is block diagram of the monitoring and control device of FIG. 3.

The monitoring and control device 43 shown in FIG. 3 will now be described in greater detail with reference to FIG. 4.

This device 43 receives the monitoring signal $S_0$ as input and includes, directly at the input, a high-pass filter 51 which makes it possible to eliminate the parasitic signals at low and medium frequencies.

It also includes a demultiplexer 53 and a differential amplifier 55, the demultiplexer 53 being controlled by the synchronisation signal $S_s$, and having for example two sampler/blockers (or analogue switches with memory) 57, 58 connecting the output of the high-pass filter 51 respectively to the inverting input of the differential amplifier 55 and to the non-inverting input thereof. Each switch 57, 58 is provided with a memory means 60, for example in the form of a capacitive component connected to a reference line of 0 Volt potential. The synchronisation signal $S_s$ controls the switches 57, 58 alternately for opening and closing.

The monitoring and control device 43 includes, connected to the output of the differential amplifier 55, an integrating circuit 61 of conventional structure which it is unnecessary to describe in detail here, which produces an integrated signal over one or several periods of the synchronisation signal. This signal constitutes the measurement signal $S_m$ and the control signal $S_c$.

The operation of the device previously described will be better understood with reference to FIGS. 5A, 5B, 5C and 5D.

Figure 5A:
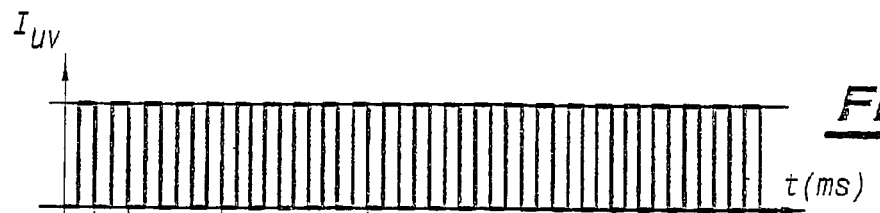
FIGS. 5A, 5B, 5C, 5D show the development over time, within a measurement interval, of the light intensities respectively of the ultraviolet analysis beam, the red reference beam, the fluorescent radiation detected at the sample output, and the amplitude of the control signal of the second light source.
Figure 5B:

As shown in FIGS. 5A and 5B, the first and second light radiation beams are emitted by the illumination means 7 phase-shifted, more precisely in phase opposition. As the synchronisation signal $S_s$ is chosen at a frequency of 1 kHz, the light signals are periodic in slots of period $T_p$ equal to 1 ms, the intensity of each radiation beam being maximum over one half-period and zero over the other half-period.

The amplitude of the light intensity of the ultraviolet analysis radiation is constant, as has already been mentioned previously, whilst the amplitude of the light intensity of the red reference radiation (from the second light source) is regulated.

A phase of maximum intensity of the UV radiation (or analysis radiation) corresponds to a zero intensity of the red radiation (or reference radiation), and vice versa.

The following time intervals are defined:
- a measurement interval $T_m$ over which the actual measurement is carried out, preferably corresponding to a large number of periods $T_p$. The duration of measurement Tm is chosen in such a way as to have a good reproducibility of measurement with the aid of sufficient averaging carried out by the computer means 33, which may be analogue or digital. In the example under consideration this is 600 ms;
- an integration time $T_i$ of at least one period $T_p$, preferably of a duration much less than that of the measurement interval $T_m$. In the example under consideration, $T_i$ has a duration equal to five periods $T_p$, namely 5 ms;
- a stabilisation interval $T_s$, which will be explained below.

The regulation is carried out in such a way that, over the integration period $T_i$, the intensity of the fluorescent radiation $I_F$ which is picked up, in this case summed, over the emission phases of the UV radiation is equal to the intensity of the fluorescent radiation $I_F$ picked up, in this case summed, over the emission phases of the red radiation.

Figure 5C:
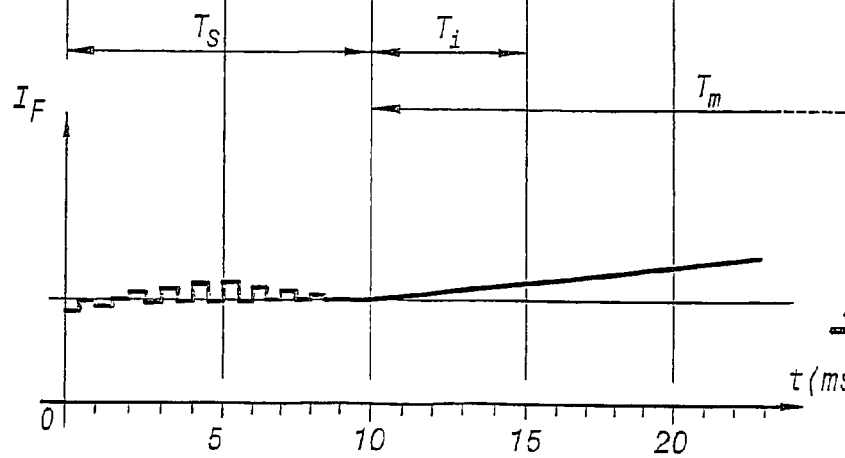

FIG. 5C shows the development of the fluorescent intensity $I_F$ (or intensity of the output radiation), and it will be seen that after the stabilisation interval $T_S$, $I_F$ varies slowly and almost continuously in such a way that it no longer exhibits rapid variations due to the alternation of the light sources. This is the result sought by the regulation loop described below.

For this the monitoring signal $S_0$ at the output of the filter 51 is "demultiplexed", that is to say broken down into a first elementary signal $S_{e1}$, directed to the inverting input of the differential amplifier 55 and a second elementary signal $S_{e2}$ directed towards the non-inverting input of the differential amplifier 55. Over an emission phase of the first radiation beam (UV radiation), that is to say for maximum $I_{UV}$, the first switch 57 is closed and the second switch 58 is open. Conversely, over an emission phase of the second radiation beam (red radiation), that is to say for maximum $I_R$ and zero $I_{UV}$, the second switch 58 is closed whilst the first switch 57 is open. By virtue of the memory means 60 the elementary signals $S_{e1}$, $S_{e2}$ at each moment represent the amplitude of intensity of the respective radiation $I_{UV}$, $I_R$ detected over the corresponding half-period.

The integrating circuit 61 integrates over the integration time period $T_i$ an alternating signal which represents, in its positive phases, the difference between the intensity of the reference radiation and the intensity of the analysis radiation during the preceding half-period and, in its negative phases, the difference between the intensity of the analysis radiation and the intensity of the reference radiation during the preceding half-period. The integration of the output signal of the differential amplifier 55 supplies a differential signal representing the difference in the contributions of the analysis radiation, on the one hand, and the reference radiation, on the other hand, in the fluorescent radiation detected.

The regulation aims to reach and to maintain an intensity value of the reference radiation such that this differential value is zero on average over the integration period, in spite of the possible variations of the fluorescence yield induced by the illumination means.

The expression of the absorbance of the sample then becomes, based on the equation given in the introduction to this application:

$$A = -\text{Log}[F1/F0 \times (I0.k0)/(I1.k1)] = -\text{Log}[1 \times (I0.k0)/(I1.k1)]$$

that is to say, identifying $I_R$ at I0: $A = -\text{Log}(I_R) + K$, where K is an instrumental constant which does not vary from one measurement to another.

The measurement signal $S_m$, which is equal here to the control signal $S_c$, is therefore directly representative of the absorbance of the sample due to the phenylpropanoid present in the epidermis.

As is shown in FIGS. 5B and 5C, the device brings the radiation intensity $I_R$ to an amplitude value such that the output radiation has the intensity $I_F$ exhibiting a slow and continuous development at the end of a stabilisation time interval $T_S$ of the regulation loop. The regulation loop is designed to reach this balance at the end of a relatively short time interval $T_S$, namely for example about ten periods $T_P$.

From this instant, the amplitude of the intensity $I_R$ is maintained substantially constant, even in the event of substantial variation in the output intensity $I_F$ induced by the illumination means or by a modification of the experimental conditions.

Figure 5D:
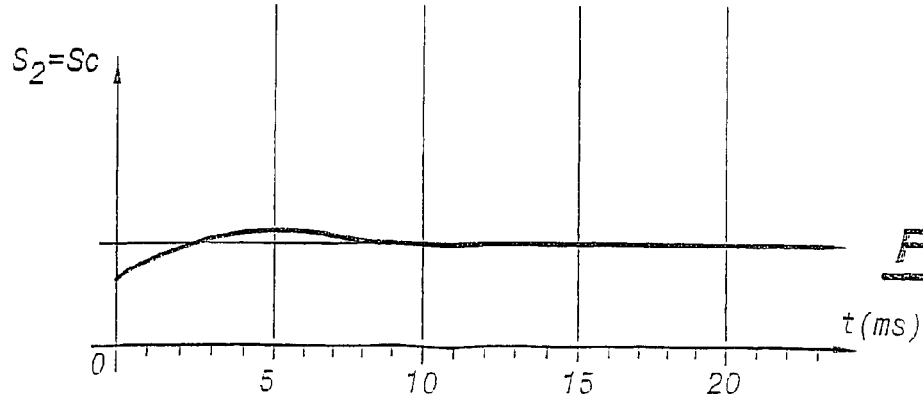

FIG. 5D shows the corresponding development of the control signal $S_C$ as a function of the time, namely the development of the control signal $S_2$ for the supply means 16 of the red source 12.

The measurement of the absorption characteristics is given, as has been seen, by the value of $I_R$ picked up on average over this measurement interval, that is to say by the (average) amplitude of the control signal $S_2$ (or $S_C$).

Finally, we should specify that the intensity $I_{UV}$ of the UV radiation is preferably constant from one measurement to another, for the sake of simplicity of the device, whilst the intensity $I_R$ of the red light is constant within the measurement interval but variable from one measurement to another.

It goes without saying that analogous regulation and results can be obtained by keeping constant not the analysis (UV) radiation but the reference (red) radiation.

Figure 6:
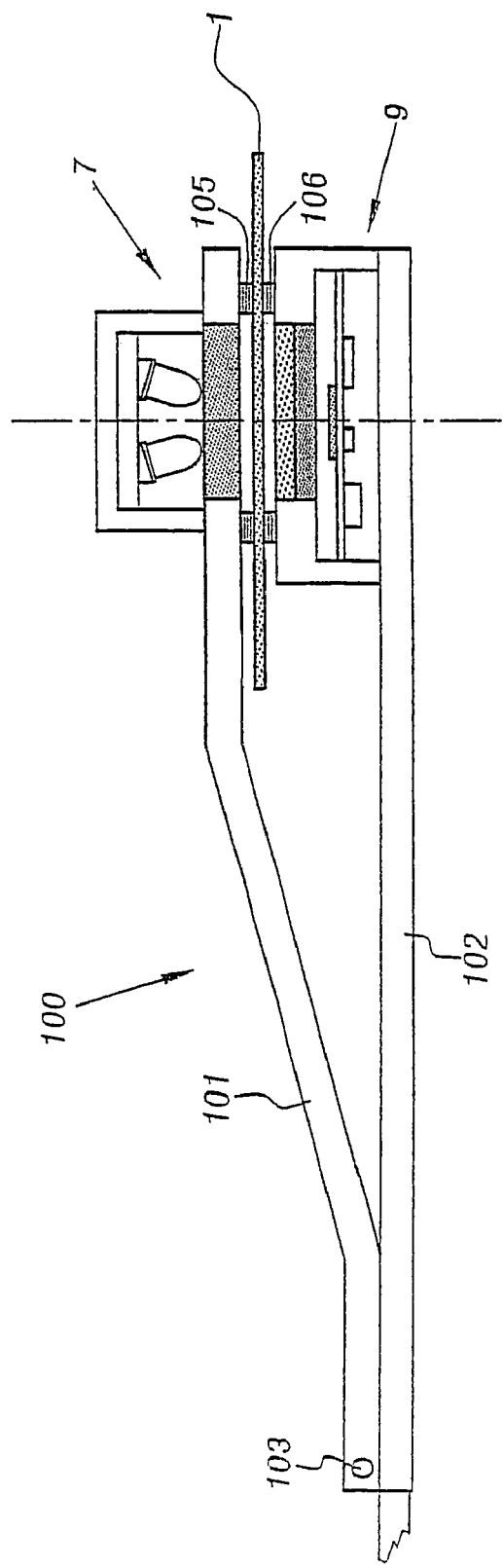
FIG. 6 illustrates a first particular embodiment of the device of FIG. 1.
Figure 7:
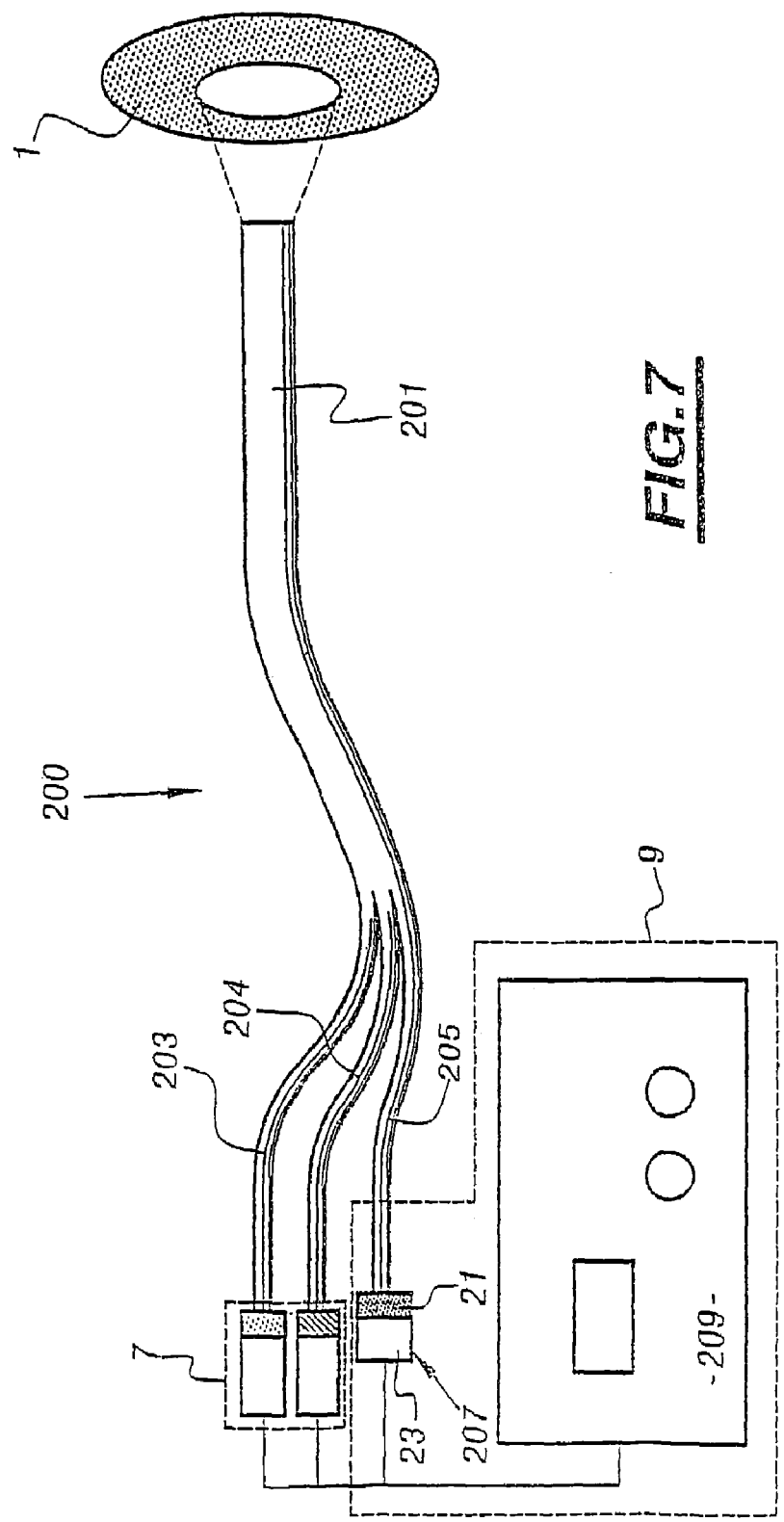
FIG. 7 illustrates a second particular embodiment of the device of FIG. 1.

FIGS. 6 and 7 show two particular embodiments of the invention.

In FIG. 6 the device takes the form of a pincer 100 having two arms 101, 102 articulated at the level of a pivot joint 103. The first arm 101 is provided with the illumination means 7, whilst the second arm 102 is provided with the reception and analysis means 9.

Each of the arms 101, 102 is also provided with a respective annular seal 105, 106 made from opaque resilient material which are disposed facing one another in such a way that when the arms 101, 102 are in the closed position they ensure sufficient darkness in the region of the sample 1 to avoid disruptions due to ambient light and to avoid any contact between the sample 1 and the hard parts of the apparatus which could damage it.

Thus such a device is particularly adapted in order to carry out very rapidly measurements in vivo on samples such as plant leaves.

According to a second particular embodiment of the invention shown in FIG. 7, the device 200 can have a bundle of optical fibres 201. The bundle of optical fibres 201 includes three secondary beams 203, 204 and 205 of which the first two 203, 204 are connected to the illumination means 7, individually to each light source, and the third is connected to the reception and analysis means 9, in particular to a sub-assembly 207 including the second optical filter 21 and the converter means 23. The sub-assembly 207 is connected electrically to an instrument 209 comprising the monitoring and control means, the computer and the peripheral.

During a measurement, one end of the bundle 201 is brought into the vicinity of the sample 1, and the bundle transmits light rays emitted by the illumination means 7 to the sample 1 and transmits the reflected ray emitted by the sample 1, in the opposite direction, to the sub-assembly 207.

Figure 8:
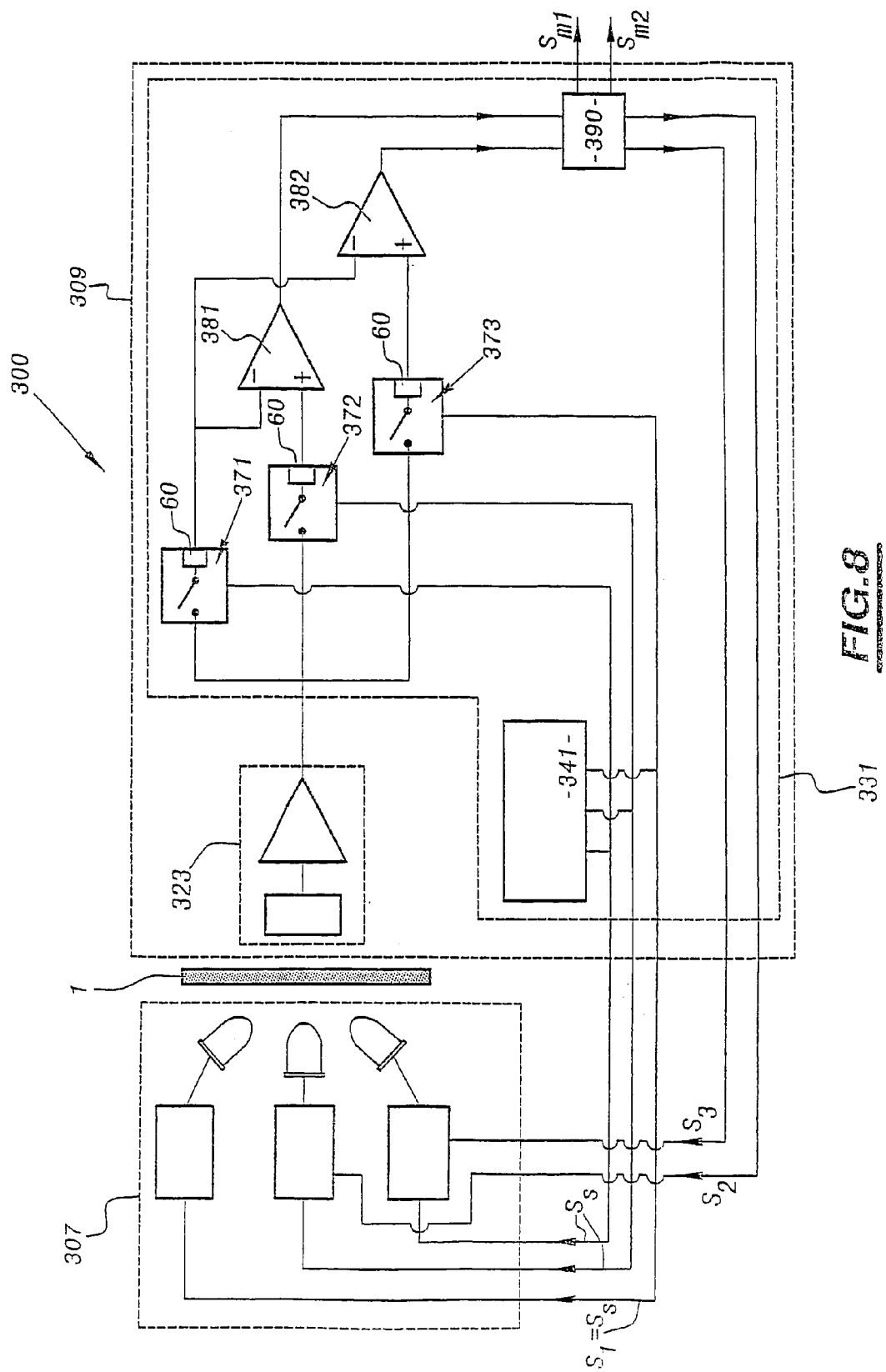
FIG. 8 shows a variant according to the invention of the device shown in FIG. 1.

FIG. 8 shows a device 300 corresponding to a particular embodiment of the invention in which there are more than two light sources, in this case three light sources emitting at different wavelengths.

For example, one of the light sources emits in the red range, the radiation emitted by this light source constituting the reference radiation. The two other light sources can emit in the ultraviolet range, at different wavelengths, in such a way as to permit measurement of the concentration in the sample 1 of different compounds, for example two different chemical compounds of the family of phenylpropanoids, of which the absorption spectra exhibit peaks at the wavelengths of the two light sources. The illumination means which comprise these three light sources have been designated in this drawing by the reference numeral 307.

The reception and analysis means 309 are similar to those described previously, but have been simplified substantially for the sake of clarity of the diagram.

In the same way as in the embodiment according to FIG. 3, the reception and analysis means 309 include converter means 323, synchronisation means 341 connected, on the one hand, to the illumination means 307 and, on the other hand, to each of three sampler/blockers (or analogue switches with memory) 371, 372, 373. In a similar manner to that described previously, the first switch 371 is connected to the inverting input of a first differential amplifier 381, on the one hand, and to the inverting input of a second differential amplifier 382, on the other hand. The two other switches 372, 373 are each connected to the non-inverting input respectively of the first differential amplifier 381 and of the second differential amplifier 382.

The three light sources of the illumination means 307 operate in an alternating manner over each synchronisation period, that is to say that one of the sources emits at the maximum light intensity value over a third of the period, whilst the other two sources do not emit, each source emitting in a periodic manner at the same period defined by the synchronisation means 341. The amplitude of the intensity of the radiation of one of the sources is constant in the image of the UV radiation of the first embodiment, whilst the amplitude of the intensity of the radiation of the two other sources is regulated by means analogous to those of the first embodiment.

The contribution to the intensity of the fluorescent radiation detected, due to each radiation beam of which the intensity is of variable amplitude, is compared with the contribution of the radiation of constant amplitude. This difference is produced by the differential amplifiers 381, 382 and integrated over several periods of the synchronisation signal, in such a way as to establish the signals with the desired amplitude for the two sources of variable amplitude. The device which effects the integration of the differential signals and which produces the desired signals transmitted to the light sources, as well as the measurement signals $S_{m1}$, $S_{m2}$ transmitted to the computer, is designated on this diagram by the reference numeral 390. This design of this device 390 will not be described in greater detail, since the analogy with the operation of the first embodiment shown in FIG. 3 will be sufficient for an understanding of the operation. In this embodiment there are two measurement signals $S_{m1}$, $S_{m2}$ which correspond respectively to the absorbance at each of the two wavelengths under consideration.

The invention claimed is:

1. Device for measuring light absorption characteristics of a biological tissue sample comprising:
   means for illumination (7; 307) of the sample (1) adapted to emit alternately at least one first and one second light radiation beam towards the sample, said radiation beams having respectively a first and a second wavelength which are different from one another;

means (9) for reception and analysis of the output light radiation emitted by the sample (1), said reception and analysis means (9) comprising means (23) for converting said output radiation into a monitoring signal ($S_O$);

monitoring and control means (31; 331) which receive the monitoring signal ($S_O$) as input and emit at the output at least first ($S_1$) and second ($S_2$) control signals for controlling the illuminating means (7; 307), corresponding to the first and second radiation beams respectively, and at least one measurement signal ($S_m$); and means (33) for computing the absorption characteristics of the sample (1) which are adapted to receive said measurement signal ($S_m$) as input and to compute said characteristics as a function of said measurement signal ($S_m$), characterised in that said monitoring and control means (31; 331) are adapted so that the light intensity ($I_{UV}$, $I_R$) of each of the radiation beams varies in a periodic manner, phase-shifted with respect to one another, and so as to regulate at least one of the control signals (S1, $S_2$) as a function of the monitoring signal ($S_O$) in such a way that, over an integration time period ($T_i$) of at least one period ($T_p$) of variation of said radiation beams, the amplitude of said monitoring signal ($S_O$) taken over the emission phases of one of the radiation beams is equal to the amplitude of the monitoring signal ($S_O$) taken over the emission phases of the other radiation beam, and in that the measurement signal ($S_m$) represents at least one of said control signals ($S_1$, $S_2$) over the integration time period ($T_i$).

2. Measuring device as claimed in claim 1, characterised in that the monitoring and control means are adapted to deliver the first control signal ($S_1$) such that the amplitude of the light intensity ($I_{UV}$) of the first radiation beam is constant, whilst the amplitude of the second control signal ($S_2$) is regulated by said monitoring and control means (31).

3. Measuring device as claimed in claim 2, characterised in that said measurement signal ($S_m$) consists of said second signal ($S_2$) over the integration time period ($T_i$).

4. Measuring device as claimed in claim 1, characterised in that the illuminating means include first (11) and second (12) light sources which are adapted to emit the first and second radiation beams respectively and are supplied electrically by respective first (15) and second (16) electrical supply means, said supply means (15, 16) being controlled by the first and second control signals respectively.

5. Measuring device as claimed in claim 4, characterised in that at least one of the light sources (11, 12) is a light-emitting diode.

6. Measuring device as claimed in claim 4, characterised in that the first light source (11) emits the first radiation beam in a wavelength range corresponding to the ultraviolet range, particularly from 300 to 390 nm, particularly approximately 370 nm.

7. Measuring device as claimed in claim 4, characterised in that the second light source (12) emits the second radiation beam in a wavelength range corresponding to the red light range, particularly approximately 670 nm.

8. Measuring device as claimed in claim 4, characterised in that the illuminating means (7; 307) include at least one optical filter (19) adapted so as to filter the radiation beams from the light sources (11, 12) emitted towards the sample (1).

9. Measuring device as claimed in claim 1, characterised in that the monitoring and control means (31; 331) include synchronisation means (41) connected to the illuminating means (7), emitting at least one periodic synchronisation signal ($S_s$) towards said illuminating means (7) in such a way that the light intensity ($I_{UV}$, $I_R$) of each of the radiation beams varies in a periodic manner, phase-shifted with respect to one another.

10. Measuring device as claimed in claim 9, characterised in that the synchronisation means (41) are adapted so as to cause the light intensity ($I_{UV}$, $I_R$) of the first and second radiation beams to vary with a frequency greater than a minimum value substantially equal to 1 kHz.

11. Measuring device as claimed in claim 9, characterised in that the monitoring and control means (31; 331) include a monitoring and control device (43) connected to the synchronisation means (41) in such a way as to receive the synchronisation signal ($S_s$), receiving the monitoring signal ($S_O$) as input.

12. Measuring device as claimed in claim 11, characterised in that said monitoring and control device includes a high-pass filter (51) adapted so as to filter the monitoring signal ($S_O$) at the input.

13. Measuring device as claimed in claim 11, characterised in that said monitoring and control device (43) includes a demultiplexer device (53) which receives as input, on the one hand, a signal representing the monitoring signal ($S_O$) and, on the other hand, the synchronisation signal ($S_s$), said demultiplexer device being adapted so as to supply as output a first elementary signal ($S_{e1}$) representing the level of intensity of the output radiation ($I_F$) during an emission phase of the first radiation beam and a second elementary signal ($S_{e2}$) representing the level of intensity of the output radiation during an emission phase of the second radiation beam.

14. Measuring device as claimed in claim 13, characterised in that the demultiplexer device (53) includes at least two switch means (57, 58) controlled alternately for opening and closing by the synchronisation signal ($S_s$), and a memory means (60) associated with each of said switch means (57, 58).

15. Measuring device as claimed in claim 13, wherein the monitoring and control device includes a high-pass filter (51) adapted so as to filter the monitoring signal ($S_O$) at the input, and wherein the signal representing the monitoring signal ($S_O$) is the monitoring signal filtered by said highpass filter (51).

16. Measuring device as claimed in claim 13, characterised in that the monitoring and control device (43) includes a differential amplifier (55) of which the inverting input receives the first elementary signal ($S_{e1}$) and the non-inverting input receives the second elementary signal ($S_{e2}$).

17. Measuring device as claimed in claim 16, characterised in that the monitoring and control device (43) includes an integrating circuit (61) which is supplied as input with the output signal from said differential amplifier (55) and is adapted so as to emit an integrated signal over at least one period of the synchronisation signal ($S_s$).

18. Measuring device as claimed in claim 17, characterised in that said integrated signal constitutes the measurement signal ($S_m$).

19. Measuring device as claimed in claim 1, characterised in that the converter means (23) include a photodetector (25) which converts an optical signal into an electrical signal and a preamplifier (27) of the electrical signal emitted by said photodetector (25).

20. Measuring device as claimed in claim 1, characterised in that the reception and analysis means (9) include an optical filter (21) interposed between the sample (1) and the converter means (23).

21. Measuring device as claimed in claim 1, characterised in that the computing means (33) are connected at the output to at least one peripheral (35), particularly a display screen and/or a data storage device.

22. Measuring device as claimed in claim 1, characterised in that the illumination means (307) are adapted so as to emit alternately three radiation beams of different wavelengths, the monitoring and control means (331) being adapted to deliver three corresponding control signals ($S_1$, $S_2$, $S_3$), the first control signal ($S_1$) being such that the amplitude of the light intensity of the first radiation beam is constant, whilst the respective amplitudes of the second control signal ($S_2$) and third ($S_3$) control signal are regulated by said monitoring and control means (331).

23. Measuring device as claimed in claim 1, characterised in that it has a pincer structure (100) comprising two arms (101, 102) articulated on one another in such a way as to be able to grip a sample, the first arm (101) being provided with the illumination means (7) and the second arm (102) being provided with the reception and analysis means (9).

24. Measuring device as claimed in claim 1, characterised in that it includes a bundle of optical fibres (201) through which the radiation beam emitted by the illumination means (7) and the radiation beam emitted by the sample (1) pass, this latter radiation beam being a reflected radiation beam.

25. Method of measuring the light absorption characteristics of a biological tissue sample, in which the following operations are carried out:

the sample (1) is illuminated by illumination means (7; 307) alternately by first and second radiation beams of different wavelengths and periodic intensities ($I_{UV}$, $I_R$);

the radiation emitted by the sample (1) is detected and said radiation is analysed;

said illumination means (7; 307) are controlled as a function of said detected radiation, characterised in that said control is carried out in the following manner:

the intensity of the first and second radiation beams ($I_{UV}$, $I_R$) is regulated such that, over an integration time period ($T_i$) of at least one period ($T_p$) of variation of said radiation beams, the intensity ($I_F$) of the output radiation taken over the emission phases of one of the first and second radiation beams is equal to the intensity ($I_F$) of the output radiation taken over the emission phases of the other one of the first and second radiation beams; and the light absorption characteristics of the sample are calculated as a function of the desired intensity of one ($I_R$) of said first and second radiation beams taken over a measurement time interval ($T_m$).

26. Method as claimed in claim 25, characterised in that the amplitude of the intensity ($I_{UV}$) of one of said first and second radiation beams is kept constant, whilst the amplitude of intensity ($I_R$) of the other one of said radiation beams is regulated.

27. Method as claimed in claim 25, characterised in that the radiation emitted by the sample (1) is filtered before it is analysed.

28. The method as claimed in claim 25, wherein the method is performed to measure the light absorption characteristics of a plant leaf, in particular in order to carry out the measurement of the concentration of compounds of the family of phenols or phenylpropanoids in the epidermis of a leaf.

29. The method as claimed in claim 25, wherein the method is performed in order to estimate the nutritional needs, particularly in terms of nitrogen, of a culture.

30. The method as claimed in claim 25, wherein the method is performed in order to measure the light absorption characteristics of an animal or human tissue containing hemoglobin derivatives.

31. The method as claimed in claim 25, wherein the method is performed to carry out a medical or veterinary diagnosis.

* * * * *